(12) United States Patent
Argentine

(10) Patent No.: US 8,663,305 B2
(45) Date of Patent: Mar. 4, 2014

(54) RETRACTION MECHANISM AND METHOD FOR GRAFT COVER RETRACTION

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 654 days.

(21) Appl. No.: 12/763,903

(22) Filed: Apr. 20, 2010

(65) Prior Publication Data

US 2011/0257718 A1 Oct. 20, 2011

(51) Int. Cl.
*A61F 2/06* (2013.01)
*A61F 11/00* (2006.01)

(52) U.S. Cl.
USPC ......... 623/1.12; 623/1.11; 623/1.23; 606/108

(58) Field of Classification Search
USPC ....................................... 623/1.23, 1.11, 1.12
See application file for complete search history.

(56) References Cited

U.S. PATENT DOCUMENTS

| | | |
|---|---|---|
| 1,827,497 A | 10/1931 | Varney |
| 4,723,938 A | 2/1988 | Goodin et al. |
| 4,832,692 A | 5/1989 | Box et al. |
| 4,990,151 A | 2/1991 | Wallsten |
| 5,017,259 A | 5/1991 | Kohsai |
| 5,137,514 A | 8/1992 | Ryan |
| 5,197,971 A | 3/1993 | Bonutti |
| 5,215,523 A | 6/1993 | Williams et al. |
| 5,259,838 A | 11/1993 | Taylor et al. |
| 5,263,969 A | 11/1993 | Phillips |
| 5,344,426 A | 9/1994 | Lau et al. |
| 5,345,927 A | 9/1994 | Bonutti |
| 5,358,496 A | 10/1994 | Ortiz et al. |
| 5,415,664 A | 5/1995 | Pinchuk |
| 5,433,723 A | 7/1995 | Lindenberg et al. |
| 5,449,344 A | 9/1995 | Taylor et al. |
| 5,462,659 A | 10/1995 | Saxena et al. |
| 5,507,727 A | 4/1996 | Crainich |
| 5,507,768 A | 4/1996 | Lau et al. |
| 5,534,007 A | 7/1996 | St. Germain et al. |
| 5,571,168 A | 11/1996 | Toro |
| 5,683,451 A | 11/1997 | Lenker et al. |
| 5,693,084 A | 12/1997 | Chuter |
| 5,700,269 A | 12/1997 | Pinchuk et al. |
| 5,707,376 A | 1/1998 | Kavteladze et al. |

(Continued)

FOREIGN PATENT DOCUMENTS

| | | |
|---|---|---|
| DE | 20000659 | 5/2001 |
| EP | 1302178 | 1/2004 |

(Continued)

*Primary Examiner* — Andrew Iwamaye
*Assistant Examiner* — Leslie Coburn

(57) ABSTRACT

A stent or stent-graft delivery system includes a handle having a graft cover retractor having a screw gear and a drive and quick release assembly. The drive and quick release assembly includes a proximal portion and a distal portion that are separable. The proximal portion of the drive and quick release assembly rotates in a first rotational direction about the screw gear to retract the graft cover using the screw gear. The drive and quick release assembly transitions from retraction using the engagement with the screw gear to retraction by sliding by the user grasping the distal portion instead of the proximal portion, and sliding the proximal portion only along the screw gear. In transitioning from using the screw gear to sliding along screw gear, it unnecessary to push any button and unnecessary for the user to remove her/his hand from the assembly.

19 Claims, 11 Drawing Sheets

(56) References Cited

U.S. PATENT DOCUMENTS

| | | |
|---|---|---|
| 5,713,917 A | 2/1998 | Leonhardt et al. |
| 5,733,267 A | 3/1998 | Del Toro |
| 5,733,325 A | 3/1998 | Robinson et al. |
| 5,755,777 A | 5/1998 | Chuter |
| 5,776,142 A | 7/1998 | Gunderson |
| 5,782,855 A | 7/1998 | Lau et al. |
| 5,788,707 A | 8/1998 | Del Toro et al. |
| 5,797,952 A | 8/1998 | Klein |
| 5,824,041 A | 10/1998 | Lenker et al. |
| 5,824,058 A | 10/1998 | Ravenscroft et al. |
| 5,860,955 A | 1/1999 | Wright et al. |
| 5,902,334 A | 5/1999 | Dwyer et al. |
| 5,906,619 A | 5/1999 | Olson et al. |
| 5,935,161 A | 8/1999 | Robinson et al. |
| 5,954,742 A | 9/1999 | Osypka |
| 5,968,052 A | 10/1999 | Sullivan, III et al. |
| 6,042,588 A | 3/2000 | Munsinger et al. |
| 6,077,297 A | 6/2000 | Robinson et al. |
| 6,110,151 A | 8/2000 | Spool et al. |
| 6,117,142 A | 9/2000 | Goodson et al. |
| 6,143,021 A | 11/2000 | Staehle |
| 6,146,415 A | 11/2000 | Fitz |
| 6,203,550 B1 | 3/2001 | Olson |
| 6,251,132 B1 | 6/2001 | Ravenscroft et al. |
| 6,395,017 B1 | 5/2002 | Dwyer et al. |
| 6,468,298 B1 | 10/2002 | Pelton |
| 6,488,700 B2 | 12/2002 | Klumb et al. |
| 6,508,790 B1 | 1/2003 | Lawrence |
| 6,514,261 B1 | 2/2003 | Randall et al. |
| 6,520,986 B2 | 2/2003 | Martin et al. |
| 6,656,212 B2 | 12/2003 | Ravenscroft et al. |
| 6,660,030 B2 | 12/2003 | Shaolian et al. |
| 6,676,692 B2 | 1/2004 | Rabkin et al. |
| 6,764,503 B1 | 7/2004 | Ishimaru |
| 6,843,802 B1 | 1/2005 | Villalobos et al. |
| 6,911,039 B2 | 6/2005 | Shiu et al. |
| 7,105,016 B2 | 9/2006 | Shiu et al. |
| 7,264,632 B2 | 9/2007 | Wright et al. |
| 7,419,501 B2 | 9/2008 | Chiu et al. |
| 7,435,253 B1 | 10/2008 | Hartley et al. |
| 7,803,177 B2 | 9/2010 | Hartley et al. |
| 7,815,671 B2 | 10/2010 | Wright et al. |
| 2002/0004676 A1 | 1/2002 | Berryman et al. |
| 2002/0111666 A1 | 8/2002 | Hart et al. |
| 2003/0074043 A1 | 4/2003 | Thompson |
| 2003/0074045 A1 | 4/2003 | Buzzard et al. |
| 2003/0199966 A1 | 10/2003 | Shiu et al. |
| 2003/0233140 A1 | 12/2003 | Hartley et al. |
| 2004/0093063 A1 | 5/2004 | Wright et al. |
| 2004/0127912 A1 | 7/2004 | Rabkin et al. |
| 2005/0085888 A1 | 4/2005 | Andreas et al. |
| 2005/0137612 A1 | 6/2005 | Assell et al. |
| 2005/0228475 A1 | 10/2005 | Keeble et al. |
| 2006/0085057 A1 | 4/2006 | George |
| 2006/0276872 A1 | 12/2006 | Arbefeuille et al. |
| 2007/0135818 A1 | 6/2007 | Moore et al. |
| 2007/0156224 A1 | 7/2007 | Cioanta et al. |
| 2007/0219616 A1 | 9/2007 | Modesitt et al. |
| 2008/0077227 A1 | 3/2008 | Ouellette et al. |
| 2008/0255651 A1 | 10/2008 | Dwork |
| 2009/0254165 A1 | 10/2009 | Tabor et al. |
| 2009/0319018 A1 | 12/2009 | Moehl et al. |
| 2010/0030255 A1 | 2/2010 | Berra et al. |
| 2011/0270372 A1 | 11/2011 | Argentine |

FOREIGN PATENT DOCUMENTS

| | | | |
|---|---|---|---|
| WO | WO96/18361 | 6/1996 | |
| WO | WO2005/067819 | 7/2005 | |
| WO | WO 2005/067819 A1 * | 7/2005 | ............... A61F 2/06 |

* cited by examiner

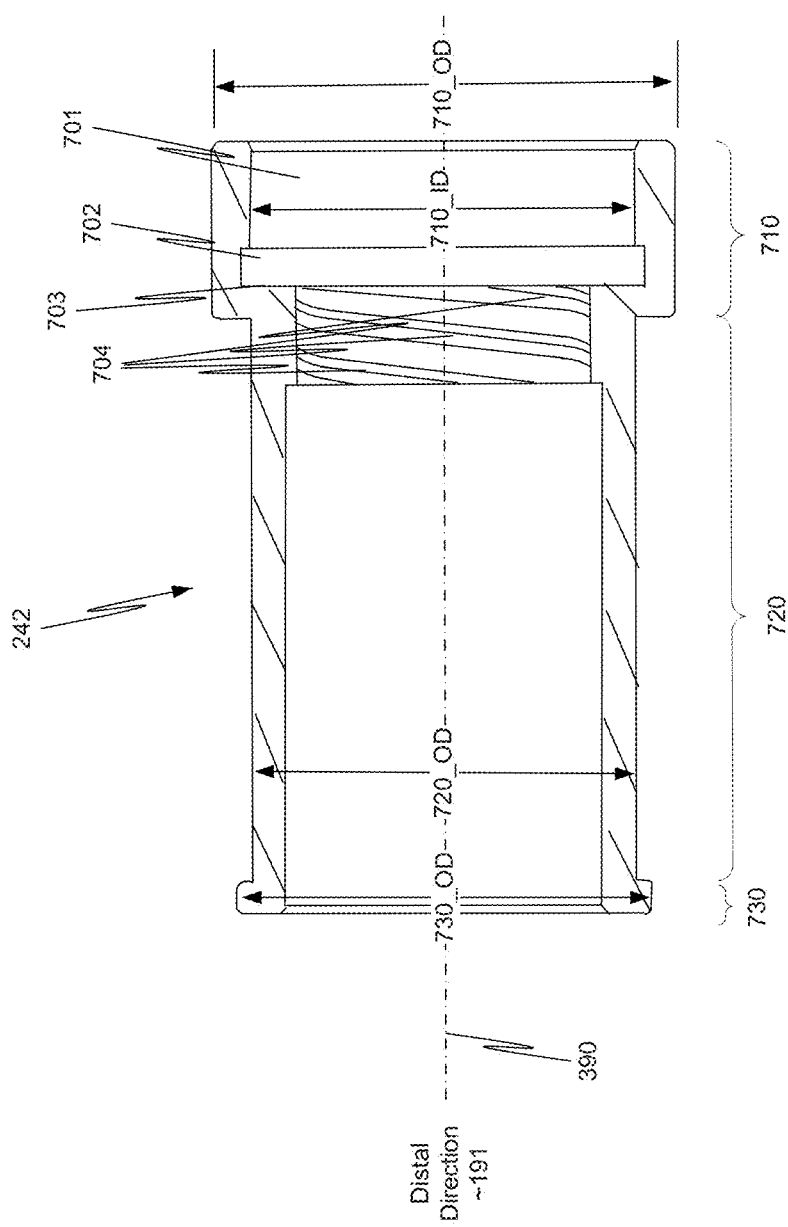

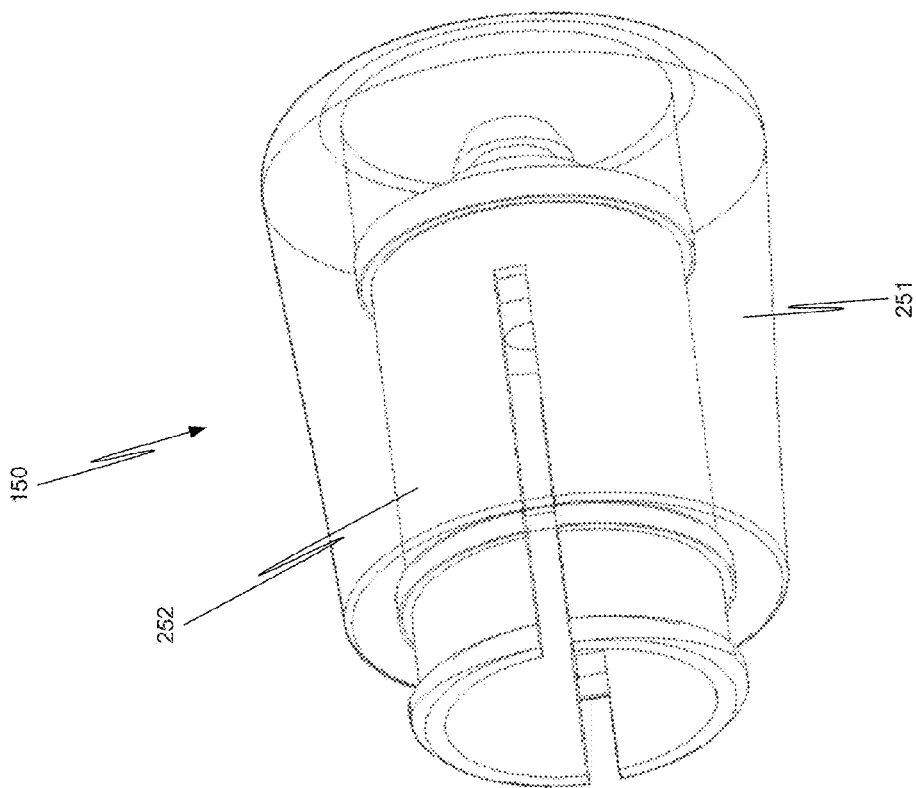

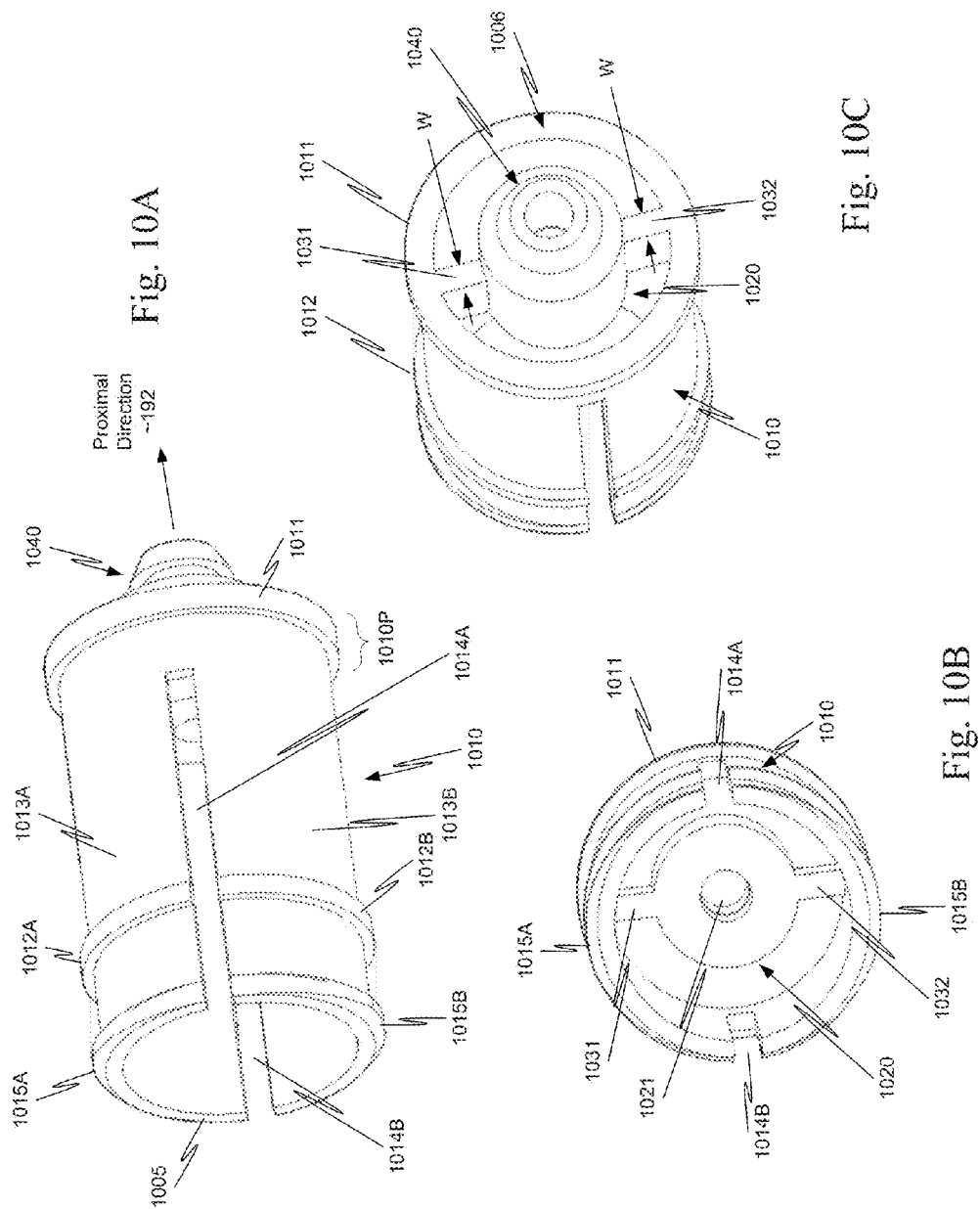

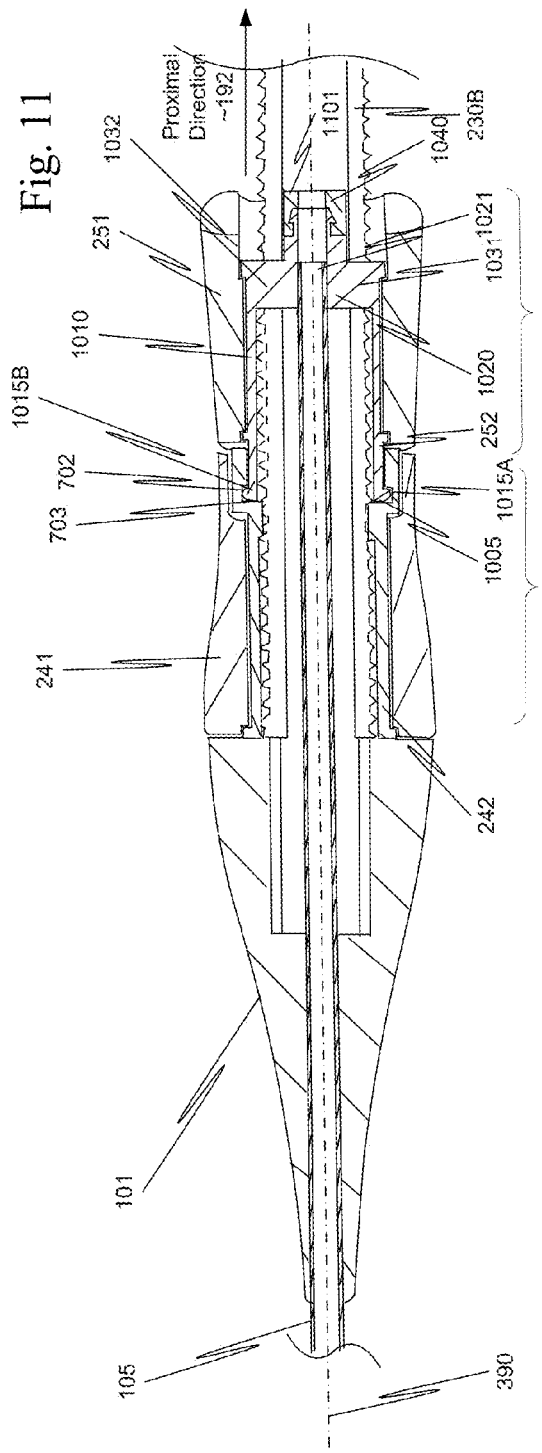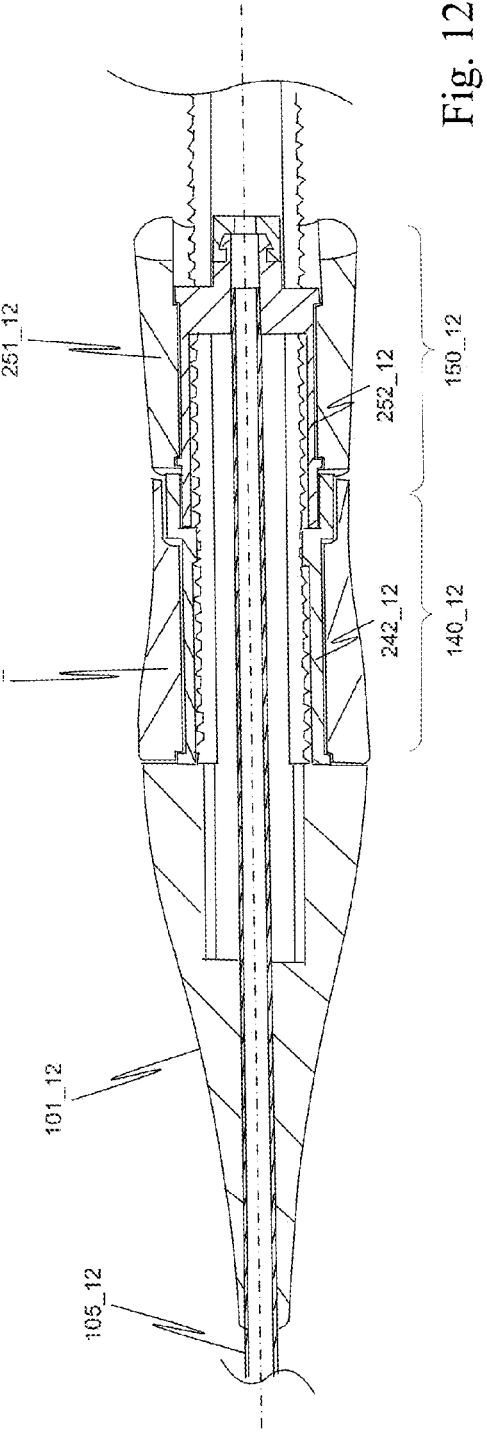

RETRACTION MECHANISM AND METHOD FOR GRAFT COVER RETRACTION

BACKGROUND

1. Field of Invention

This invention relates generally to medical devices and procedures, and more particularly to a method and system of deploying a self expanding prosthesis like a stent graft or a stent in a vascular system.

2. Related Art

Prostheses for implantation in blood vessels or other similar organs of the living body are, in general, well known in the medical art. For example, prosthetic vascular grafts formed of biocompatible materials (e.g., Dacron or expanded polytetrafluoroethylene (ePTFE) tubing) have been employed to replace or bypass damaged or occluded natural blood vessels.

A graft material supported by a framework is known as a stent-graft or endoluminal graft. In general, the use of stents and stent-grafts for treatment or isolation of vascular aneurysms and vessel walls which have been thinned or thickened by disease (endoluminal repair or exclusion) is well known.

Many stents and stent-grafts are "self-expanding", i.e., inserted into the vascular system in a compressed or contracted state, and permitted to expand upon removal of a restraint. Self-expanding stents and stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent or self-expanding stent-graft is typically configured in a tubular shape and sized to have a slightly greater diameter than the diameter of the blood vessel in which the stent or stent-graft is intended to be used. In general, rather than by treatment in a traumatic and invasive manner using open surgery, when stents and stent-grafts are used for treatment, the stent or stent-graft typically is deployed through a less invasive intraluminal delivery, i.e., cutting through the skin to access a lumen or vasculature or percutaneously via successive dilatation, at a convenient (and less traumatic) entry point, and routing the stent or stent-graft through the lumen of the vasculature to the site where the prosthesis is to be deployed.

Intraluminal deployment in one example is effected using a delivery catheter with coaxial inner tube, sometimes called an inner tube (plunger), and an outer tube, sometimes called the sheath, arranged for relative axial movement. The stent or stent-graft is compressed and disposed within the distal end of the sheath in front of the inner tube.

The catheter is then maneuvered, typically routed though a vessel (e.g., lumen), until the end of the catheter containing the stent or stent-graft is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent or stent-graft is gradually exposed. The exposed portion of the stent or stent-graft radially expands so that at least a portion of the expanded portion is in substantially conforming surface contact with a portion of the interior wall of the blood vessel.

The proximal end of the stent or stent-graft is the end closest to the heart by way of blood flow path whereas the distal end of the stent or stent-graft is the end furthest away from the heart by way of blood flow path during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the stent-graft is the end nearest the operator (the end nearest the handle or the handle itself), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the distal and proximal end descriptors for the stent-graft and delivery system description may be consistent or opposite in actual usage.

Some self-expanding stent deployment systems and stent-graft deployment systems are configured to have each exposed increment of the stent or stent graft at the proximal end of the stent-graft deploy (flare out or mushroom) as the sheath is pulled back. Thus, a surgeon must carefully and deliberately apply a controlled force to retract the sheath in a controlled and predictable manner.

SUMMARY

In one example, a stent or stent-graft delivery system includes a graft cover retractor. The graft cover retractor includes a screw gear including at least one longitudinal slot, and a drive and quick release assembly coupled to the screw gear. The screw gear is sometimes referred to herein as a slotted hollow screw gear. The drive and quick release assembly includes a proximal portion and a distal portion that are separable.

The distal portion of the drive and quick release assembly rotates in a first rotational direction about the screw gear to retract the graft cover using the screw gear. The drive and quick release assembly transitions from retraction using the engagement with the screw gear to retraction by sliding by the user grasping the proximal portion instead of the distal portion, and sliding the proximal portion only along the screw gear.

The transition from using engagement with the screw gear to sliding retraction does not require the use of button; does not require looking away from a viewing screen; and does not require removing the hand from the drive and quick release assembly. Thus, the graft cover retractor eliminates cumbersome steps required in the operation of some conventional graft cover retraction assemblies.

In one example, the graft cover retractor includes (i) a screw gear including at least one longitudinal slot; and (ii) a drive and quick release assembly, coupled to the screw gear. The drive and quick release assembly includes (a) a screw gear drive assembly having a proximal end edge surface; and (b) a graft cover anchor assembly having a distal end edge surface abutting the proximal end edge surface of the screw gear drive assembly, and affixed to a graft cover. When the screw gear drive assembly is rotated about the screw gear in a first rotational direction, longitudinal motion of the screw gear drive assembly moves the graft cover anchor assembly in a proximal direction to retract the graft cover. The graft cover anchor assembly is separated from the screw gear drive assembly by grasping the graft cover anchor assembly and sliding the graft cover anchor assembly away from the screw gear drive assembly. Only grasping and sliding are needed to separate the graft cover anchor assembly from the screw gear drive assembly.

In another example, the graft cover retractor includes (i) a hollow slotted screw gear, (ii) a hollow graft cover advance nut mounted on the screw gear, and (iii) a spacer graft cover anchor. The hollow slotted screw gear includes a first screw gear part, and a second screw gear part. A first separation between the first screw part and the second screw gear part defines a first longitudinal slot. A second separation between the first screw part and the second screw gear part defines a second longitudinal slot.

The hollow graft cover advance nut is sometimes referred to herein as a graft cover advance nut. The hollow graft cover advance nut includes a first inner surface and a second inner surface distal to the first inner surface. The hollow graft cover advance nut also includes a proximal end edge surface positioned between the first inner surface and the second inner surface, and threads extending from the second inner surface. The hollow slotted screw gear is mounted within the hollow graft cover advance nut so that threads of the hollow slotted screw gear engage the threads of the hollow graft cover advance nut.

The spacer graft cover anchor, sometimes referred to herein as the graft cover anchor, includes a distal end configured to removably fit within the proximal end of the hollow graft cover advance nut between threads of the hollow slotted screw gear and the first inner surface of the hollow graft cover advance nut. The spacer graft cover anchor is affixed to a graft cover.

When (i) the distal end of the spacer graft cover anchor is within the proximal end of the hollow graft cover advance nut and is in contact with the proximal end edge surface of the hollow graft cover advance nut, and (ii) the hollow graft cover advance nut is rotated about the hollow slotted screw gear in a first rotational direction, the graft cover is retracted. When the spacer graft cover anchor is slid in a proximal direction longitudinally along the hollow slotted screw gear and the distal end of the spacer graft cover anchor is within the proximal end of the hollow graft cover advance nut, the distal end of the spacer graft cover anchor is removed from within the proximal end of the hollow graft cover advance nut, and the graft cover also is refracted by the sliding.

In one example, the hollow slotted screw gear, the hollow graft cover advance nut, and the spacer graft cover anchor, each have a longitudinal axis that is coincident with a longitudinal axis of the handle of the graft delivery system and so are said be coaxial. Also, the hollow graft cover advance nut, in one example, is a single integral part. Integral, as used herein, means that the part is only one piece and is not multiples pieced joined together to form the part. Similarly, in one example, the spacer graft cover anchor is a single integral part that is molded on the graft cover.

The proximal end of the hollow graft cover advance nut includes a proximal portion having an inner circumferential surface bounding a volume. The inner circumferential surface is the first inner surface of the hollow graft cover advance nut. The proximal end edge surface is located at a distal end of the volume, and a proximal end of the volume is open. The second inner surface and the threads extending from the second inner surface are distal to the proximal end edge surface of the graft cover advance nut.

The graft cover anchor includes an outer body, extending around the screw gear. An inner body of the graft cover anchor is positioned within the screw gear and is affixed to a graft cover. A first spacer of the graft cover anchor extends through the first longitudinal slot, and connects the inner body to the outer body. Similarly, a second spacer of the graft cover anchor extends through the second slot, and connects the inner body to the outer body.

In one example the outer body further includes a plurality of cantilevered beams. Each cantilevered beam extends in a distal direction from a proximal end portion of the outer body. Each cantilevered beam includes a distal end edge surface. The distal end of the spacer graft cover anchor assembly comprises the distal end of the cantilevered beam.

In a further example, each cantilevered beam includes an engagement tab at a distal end of the cantilevered beam. The engagement tab extends radially out from an outer surface of the cantilevered beam. In this example, the graft cover advance nut includes a recessed groove formed in the inner circumferential surface adjacent to and proximal to the proximal end edge surface of the graft cover advance nut. The engagement tab at the distal end of the cantilevered beam latches in the recessed groove so that the distal end edge surface of the cantilevered beam contacts the proximal end edge surface of the graft cover advance nut. However, when the graft cover anchor is latched to the hollow graft cover advance nut, the hollow graft cover advance nut is still free to rotate about the portion of the graft cover anchor within the proximal end of the hollow graft cover advance nut.

In another example, the outer body includes a hollow cylinder extending distally from the proximal end portion of the outer body. The hollow cylinder includes a distal end edge surface. The distal end edge surface of the outer body abutting the proximal end edge surface of the screw gear drive assembly includes the distal end edge surface of the hollow cylinder.

A method of operating a graft delivery system includes grasping a distal portion of a drive and quick release assembly and rotating the drive and quick release assembly in a first rotational direction along a screw gear to longitudinally move a graft cover in a first direction. The method also includes changing the grasping to a proximal portion of the drive and quick release assembly and sliding only the proximal portion of the drive and quick release assembly longitudinally along the screw gear.

BRIEF DESCRIPTION OF THE DRAWINGS

FIG. 7C is a cross sectional view of the graft cover advance nut, e.g., along a cut line 7C-7C in FIG. 7B.

FIG. 8 is an oblique see through view of the graft cover anchor assembly.

FIG. 10A is an oblique view of the graft cover anchor including a distal end edge surface of the outer body.

FIG. 10B is an oblique distal end view of the graft cover anchor including a distal end edge surface of the outer body.

FIG. 10C is an oblique proximal end view of the graft cover anchor including a proximal end of the inner body.

FIG. 11 is a cross-sectional view of the distal portion of the handle in FIG. 2 along a cut plane extending through the longitudinal centerline of both slots in the screw gear and including the longitudinal axis.

FIG. 12 is a cross-sectional view of the distal portion of an alternative implementation (embodiment) of the handle in FIG. 2 along a cut plane extending through the longitudinal centerline of both slots in the screw gear and including the longitudinal axis.

Figure 1:
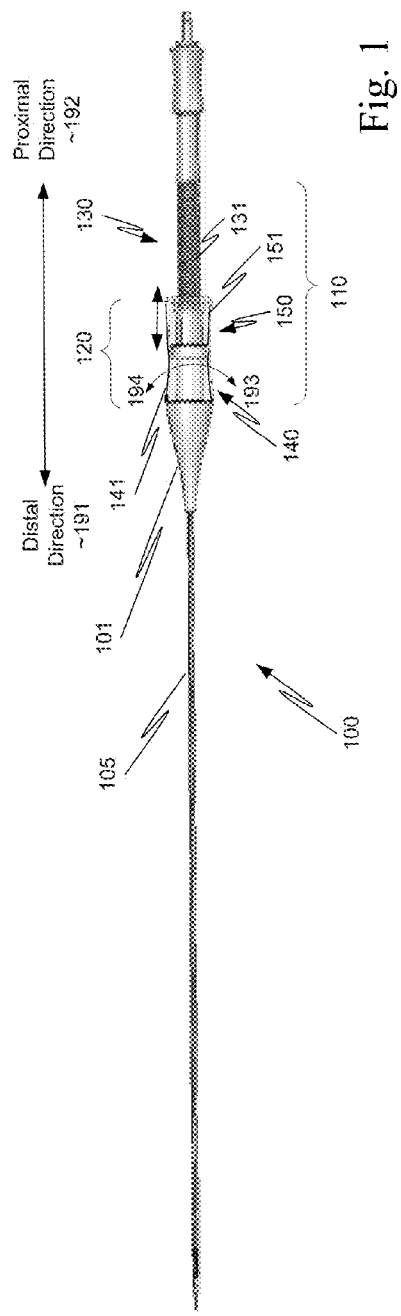
FIG. 1 is an illustration of delivery system that includes a graft cover refractor.

In the drawings, the first digit of a reference number for an element indicates the figure in which the element with that reference number first appeared.

DETAILED DESCRIPTION

Present technology for retracting a graft cover during deployment of a stent graft is adequate and functional. However, typically the conventional mechanism used in retracting the graft cover is complicated and costly. Graft delivery system 100 includes a handle having a graft cover retractor 110, which overcomes these limitations. Herein, graft delivery system 100 includes a stent delivery system and a stent graft delivery system as the implementation and use of graft cover retractor 110 is the same in both systems.

In this example, graft cover retractor 110 includes a screw gear 130, sometimes referred to herein as a hollow slotted screw gear 130, and a drive and quick release assembly 120, sometimes referred to herein as assembly 120. A distal end of screw gear 130 is fixedly attached to a distal end of the handle, i.e., fixedly attached to a contoured strain relief element 101. A proximal end of screw gear 130 is fixedly attached to a proximal end of the handle.

Drive and quick release assembly 120 includes a proximal portion 150 and a distal portion 140. Proximal portion 150 and distal portion 140 each have a longitudinal axis that is coincident with the longitudinal axis of the handle and so are coaxial components.

Figure 2:
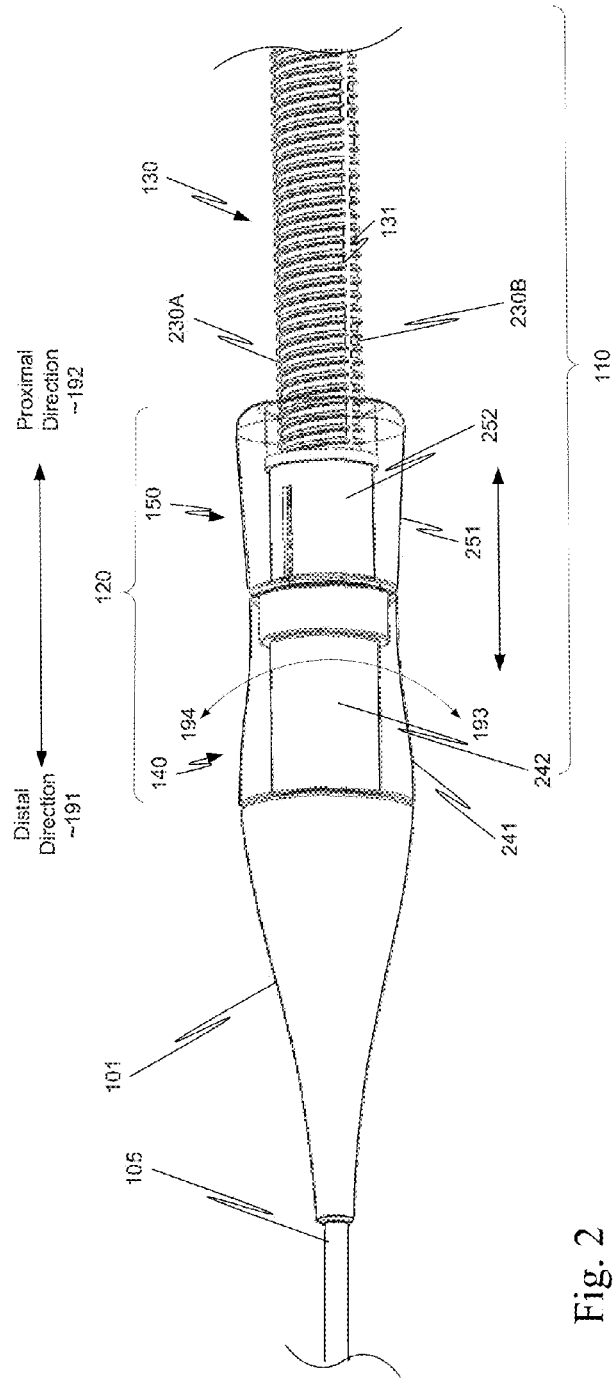
FIG. 2 is a close-up partial see through illustration of the graft cover retractor of FIG. 1.

In an initial position as illustrated in FIGS. 1 and 2, proximal portion 150 contacts distal portion 140 so that longitudinal motion of distal portion 140, along the longitudinal axis of the handle, is transferred to proximal portion 150, as explained more completely below.

Distal portion 140, sometimes referred to as screw gear drive assembly 140, is engaged with screw gear 130 and moves longitudinally as assembly 140 is rotated around screw gear 130 in a first rotation directional 193, or in a second rotation direction 194. The frictional force resisting movement between graft cover 105 and a compressed stent or compressed stent-graft is quite high and so the mechanical advantage obtained by using screw gear drive assembly 140 engaged with the threads of screw gear 130 can assist in initially moving graft cover 105. As screw gear drive assembly 140 is rotated around screw gear 130, screw gear drive assembly 140 moves longitudinally along the threads of screw gear 130.

Initially, a proximal end edge surface of screw gear drive assembly 140 contacts (abuts) a distal end edge surface of proximal portion 150, which is sometimes referred to as graft cover anchor assembly 150. Graft cover anchor assembly 150 does not engage the threads of screw gear 130 and instead surrounds and slides longitudinally along screw gear 130.

As explained more completely below, graft cover anchor assembly 150 includes a spacer for each slot 131 in screw gear 130, and the spacer slides along the slot in screw gear 130. Graft cover anchor assembly 150 also is fixedly attached to graft cover 105 so that as graft cover anchor assembly 150, sometimes referred to herein as assembly 150, slides along screw gear 130, graft cover 105 moves in unison with assembly 150.

As explained more completely below, drive and quick release assembly 120 allows a user to retract a graft cover 105 by grasping screw gear drive assembly 140 and rotating screw gear drive assembly 140 of drive and quick release assembly 120 in first rotational direction 193 about screw gear 130, e.g., counter-clockwise (viewed from the proximal end of the catheter). The rotation of screw gear drive assembly 140 in first rotational direction 193 causes screw gear drive assembly 140 to move along the threads of screw gear 130 and thereby move longitudinally in proximal direction 192. Screw gear drive assembly 140 rotates about the portion of graft cover anchor assembly 150 with assembly 140, but the longitudinal motion of screw gear drive assembly 140 (in the configuration shown) is imparted to graft cover anchor assembly 150 so that graft cover anchor assembly 150 slides longitudinally along screw gear 130 in proximal direction 192 and retracts graft cover 105.

To withdraw graft cover 105 more quickly, the user releases the grasping force on the screw gear drive assembly 140 and slides the user's hand to grasp graft cover anchor assembly 150 applying a longitudinal retracting force to slide assembly 150 in proximal direction 192. In transitioning from using (engagement with) screw gear 130 to sliding along screw gear 130, it unnecessary to push any button and unnecessary for the user to remove her/his hand from assembly 120. Rather, the user shifts the grasp from distal portion 140 to proximal portion 150 of assembly 120. In this example, the easily tactilely detectable contour of the outer surface of assembly 120 assists the user in shifting the grasp without looking at the handle.

Thus, the user does not have to look away from a viewing screen to see how to manipulate delivery system 100 to change modes of graft cover retraction. The user's hand can remain in contact with assembly 120 when retracting the graft cover, i.e., whether retracting the graft cover employing the mechanical advantage of the associated screw or pulling the graft cover back in a quick-retraction mode.

FIG. 2 is a close-up illustration of graft cover retractor 110. Screw gear 130 includes a first screw gear part 230A, and a second screw gear part 230B. First screw gear part 230A and second screw gear part 230 are configured to have portions separated by a plurality of slots of which only slot 131 is visible in FIG. 2.

Screw gear drive assembly 140 includes a contoured screw drive grip 241 and a graft cover advance nut 242 in this example. Graft cover advance nut 242, sometimes referred to herein as hollow graft cover advance nut 242, is fixedly mounted within contoured screw drive grip 241 so that the two elements function as a single element, i.e., rotation of contoured screw drive grip 241 rotates graft cover advance nut 242. The contour of the outer surface of contoured screw drive grip 241 is generally diametrically decreasing from the distal to the proximal end of the contoured screw drive grip 241.

Graft cover anchor assembly 150 includes a contoured graft cover release grip 251 and a graft cover anchor 252. Graft cover anchor 252, sometimes referred to herein as spacer graft cover anchor 252, is fixedly mounted within contoured graft cover release grip 151 so that the two elements function as a single element. Also, graft cover anchor 252 is fixedly attached to graft cover 105 i.e., moving contoured graft cover release grip 251 moves graft cover anchor 252. The contour of the outer surface of contoured graft cover release grip 251 is generally diametrically increasing from the distal to the proximal end of the contoured graft cover release grip 241.

Figure 5A:
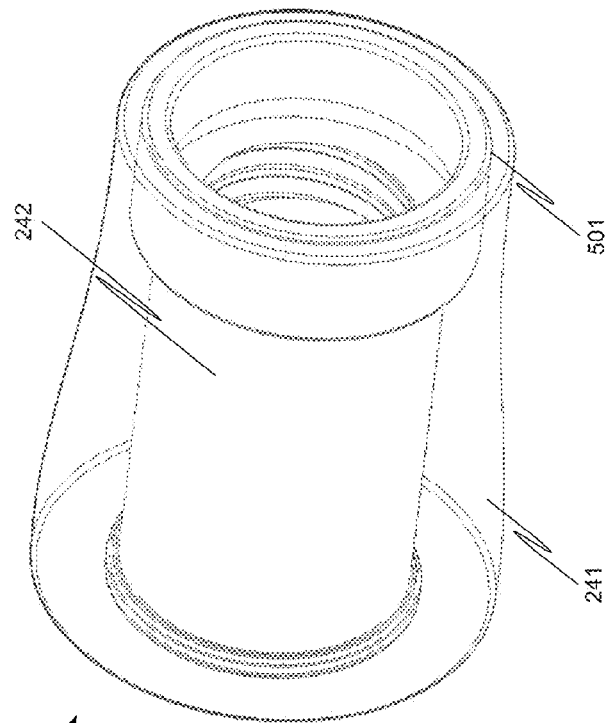
FIG. 5A is an oblique see through view of the screw gear drive assembly including a proximal end surface.
Figure 5B:
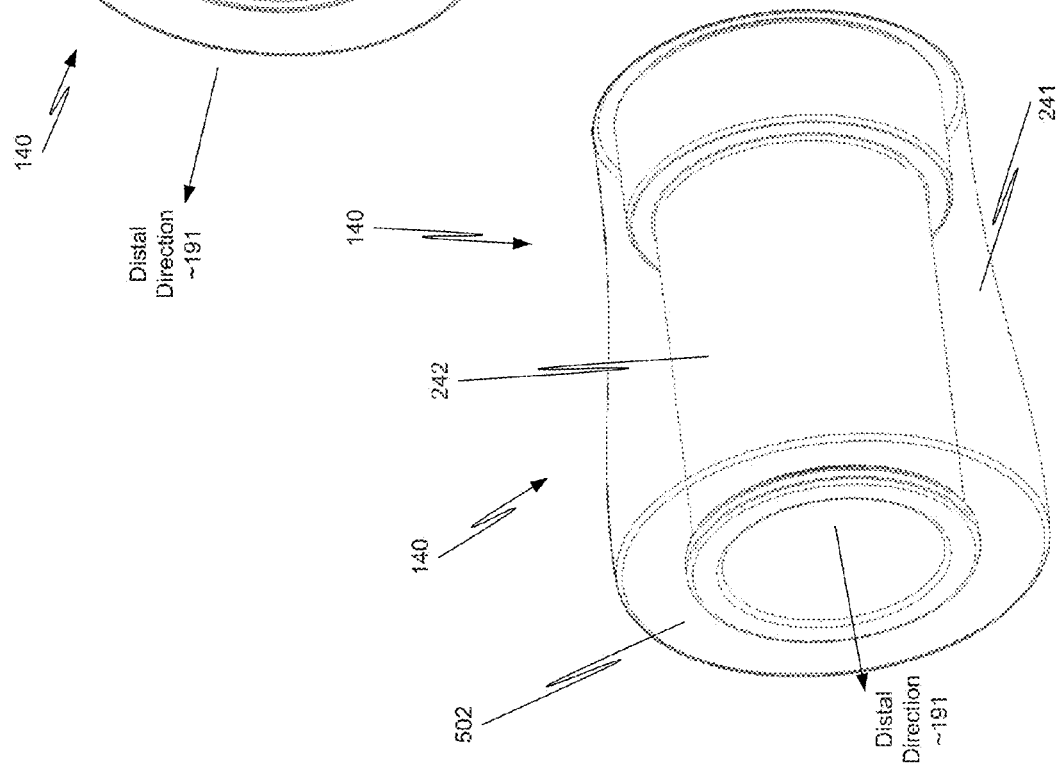
FIG. 5B is an oblique see through view of the screw gear drive assembly including a distal end surface.
Figure 6:
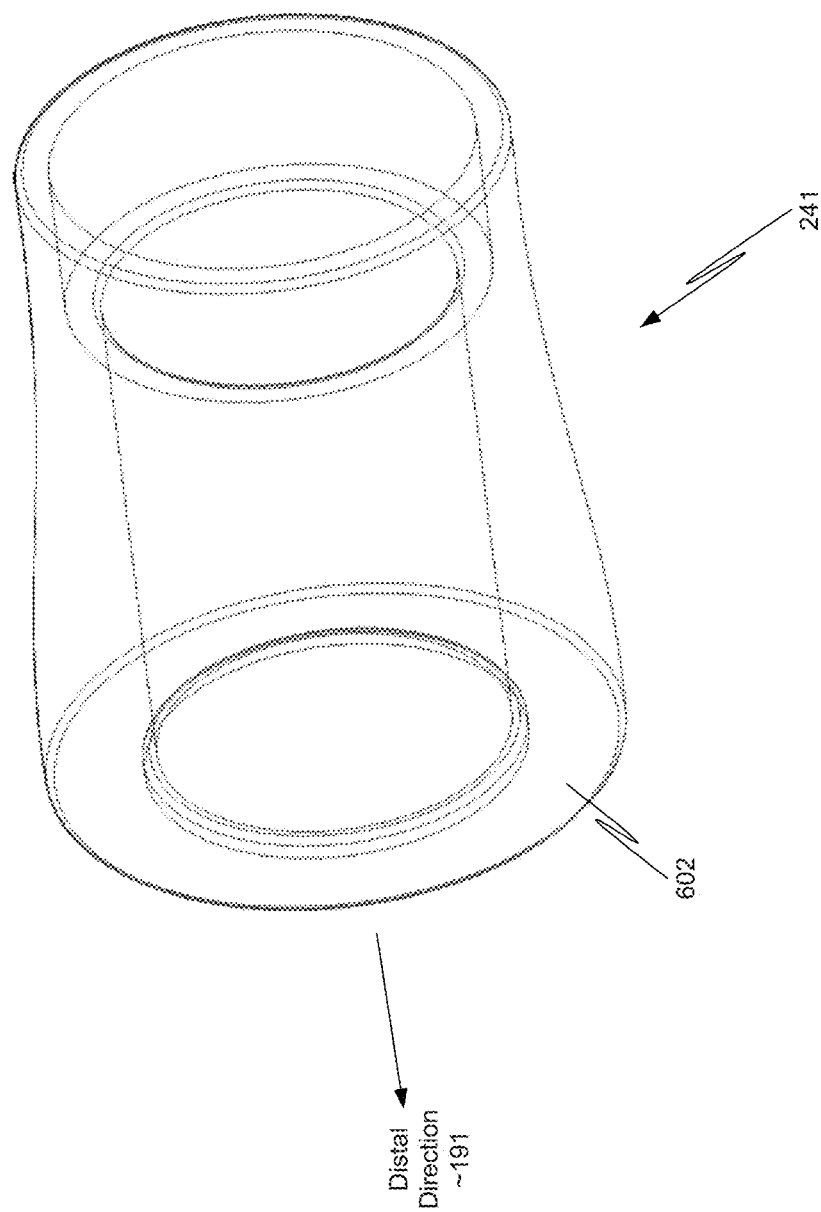
FIG. 6 is an oblique see through view of the contoured screw drive grip including a distal end surface.

In FIGS. 5A, 5B, and 6, contoured screw drive grip 241 is illustrated as a see through frame to illustrate features within contoured screw drive grip 241. However, in other examples contoured screw drive grip 241 is opaque. The transparency of contoured screw drive grip 241 is for ease of discussion only and is not limiting on the characteristics of contoured screw drive grip 141.

Figure 9:
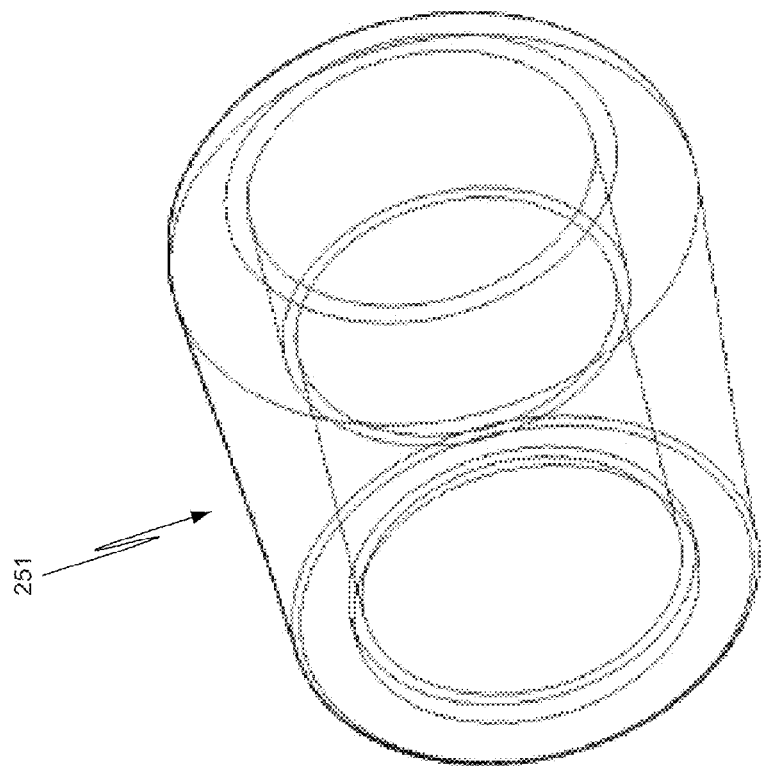
FIG. 9 is an oblique see through view of the contoured graft cover release grip.

In FIGS. 8 and 9 contoured graft cover release grip 251 is illustrated as a see through frame to illustrate features within contoured graft cover release grip 251. However, in other examples, contoured graft cover release grip 251 is opaque. The transparency of contoured graft cover release grip 251 is for ease of discussion only and is not limiting on the characteristics of contoured graft cover release grip 251.

Returning to FIG. 2, grasping contoured screw drive grip 241 and rotating screw gear drive assembly 140 in first rotational direction 193 rotates graft cover advance nut 242 about screw gear 130 and about the portion of graft cover anchor assembly 150 within assembly 140. The rotation of graft cover advance nut 242 about screw gear 130 moves screw gear drive assembly 140 longitudinally in proximal direction 192.

As described above and as shown in FIG. 2, initially, a proximal end edge surface of screw gear drive assembly 140 contacts a distal end edge surface of graft cover anchor assembly 150. Thus, as screw gear drive assembly 140 moves longitudinally in proximal direction 192, the proximal end edge surface of screw gear drive assembly 140 applies a longitudinal force to the distal end edge surface of graft cover anchor assembly 150 that causes graft cover anchor assembly 150 to slide longitudinally, in proximal direction 192, along screw gear 130.

Thus, after a number of revolutions of screw gear drive assembly 140 about and along screw gear 130, graft cover 105 has been partially retracted. Drive and quick release assembly 120 has been moved proximally relative to contoured strain relief element 101 to the position on screw gear 130 illustrated in FIG. 3A. Note that screw gear drive assembly 140 and graft cover anchor assembly 150 are still in contact with each other.

Figure 3A:
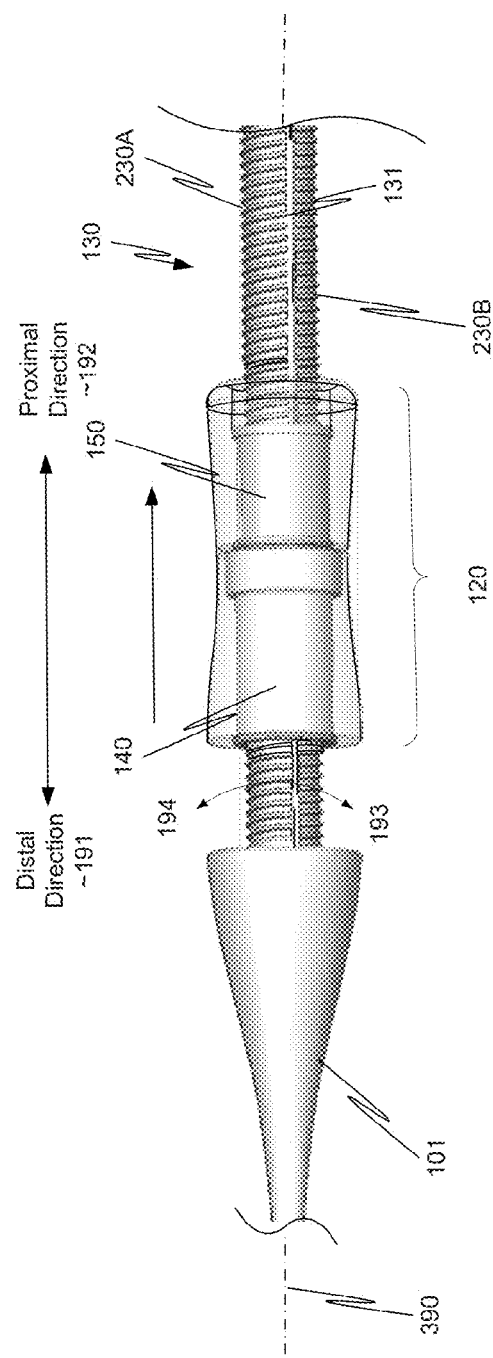
FIG. 3A is a close-up illustration of the graft cover retractor after the drive and quick release assembly has been rotated a number of revolutions.
Figure 3B:
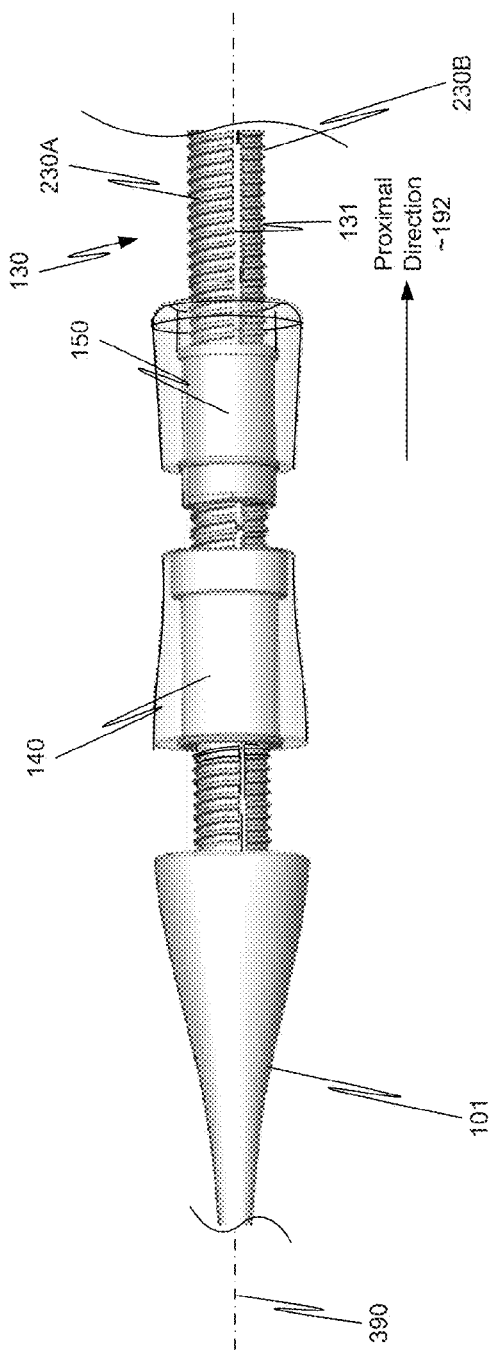
FIG. 3B is a close-up illustration of the graft cover retractor of FIG. 3A after the proximal portion of the drive and quick release assembly has been slid away from the distal portion of the drive and quick release assembly.

At the position illustrated in FIG. 3A, the mechanical advantage supplied by screw gear drive assembly 140 is no longer needed as the longitudinal force needed to retract the sheath has diminished from an initially very high force that is needed to retract the sheath when the whole length of the tightly compressed stent or stent graft is initially moved from its fully compressed and thereby maximum static frictional resistance position to a partially deployed much lower partially compressed static frictional resistance position, and the operator wants to quickly slide graft cover 105 further in proximal direction 192. To do this, the operator simply transfers his/her grasp from distal portion 140 of drive and quick release assembly 120 to grasp proximal portion 150 of assembly 120. The operator then applies a longitudinal refraction force to slide proximal portion 150 in proximal direction 192. The grasping of proximal portion 150 coupled with the application of a longitudinal force to create a sliding motion that separates proximal portion 150 from distal portion 140 causing only proximal portion 150 to move in proximal direction 192. See FIG. 3B. The sliding of proximal portion 150 causes graft cover 105 to retract more quickly than can be done by using (rapid rotation of) screw gear drive assembly 140.

If it is necessary to move graft cover 105 to its fully (or a more) distal position, distal portion 140 must also be moved to its fully (or more) distal position. As long as the proximal portion 150 is still longitudinally separated from distal portion 140 so that at least one thread on screw gear 130 is visible between the proximal end of distal portion 140 and the most distal end of proximal portion 150, the operator can grasp distal portion 140 apply force and move distal portion 140 in distal direction 191 using only a longitudinal motion.

This longitudinal motion of screw gear drive assembly 140 is possible because the spacers in graft anchor assembly 150, which prevent the sideways collapse of slot 131, are removed from screw gear drive assembly 140, when the two assemblies are not engaged and are separated by at least one thread. Thus, screw gear parts 230A, 230B can flex (elastically deflect) towards each other when a longitudinal sliding force is applied to screw gear drive assembly 140 causing the teeth of the screw threads inside the screw gear drive assembly 140 to create an inward force on the screw gear parts 230A, 230B. The internal flexing of screw gear parts 230A, 230B is not resisted by proximal portion 150 because proximal portion 150 is separated from assembly 140 so that the spacers in proximal portion 150 are not in a position to maintain the spacing between screw gear parts 230A and 230B within assembly 140 and thereby prevent the flexing.

After screw gear drive assembly 140 is moved to its desired location, graft cover anchor assembly 150 can be slid in distal direction 191 to move graft cover 105 in distal direction 191. Graft cover anchor assembly 150 can be slid in distal direction 191 until graft cover anchor assembly contacts screw gear drive assembly 140.

Screw Gear 130

Figure 4:
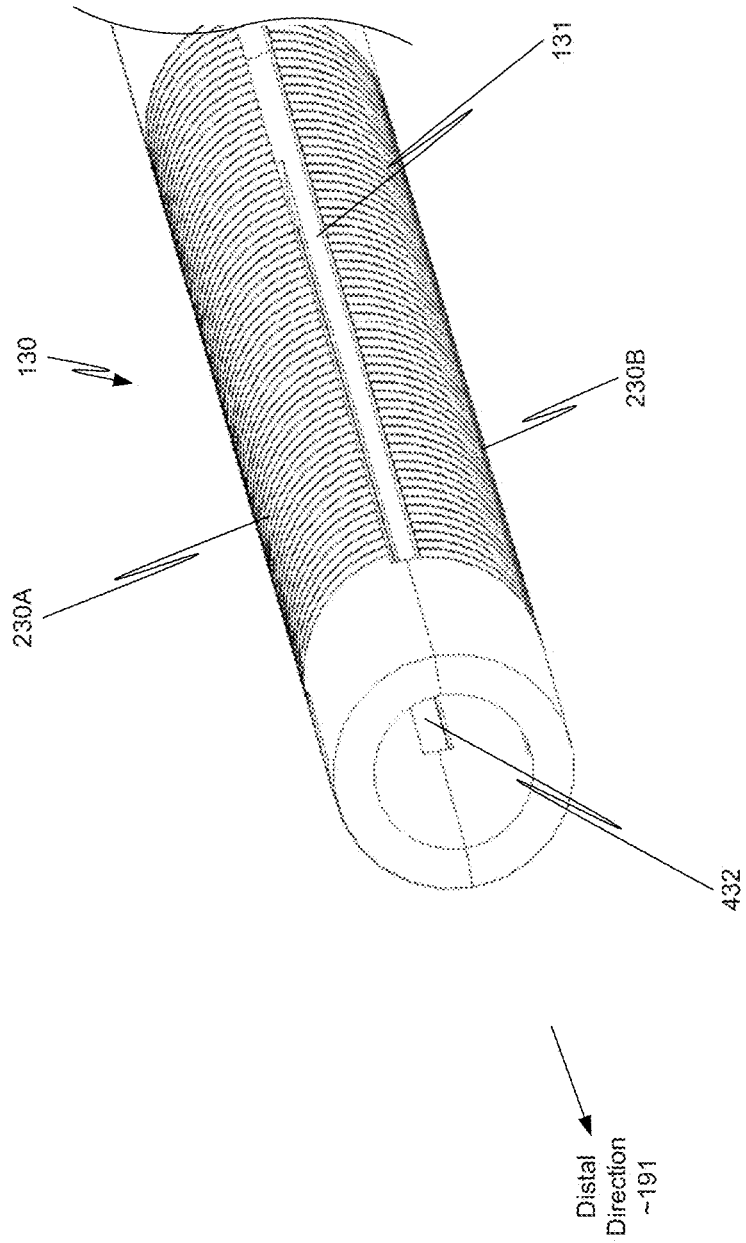
FIG. 4 is an oblique non contoured boxed cylinder side view illustration of the screw gear.

FIG. 4 is an oblique non contoured boxed cylinder side view illustration of screw gear 130 separate from other parts. As described above screw gear 130 includes a first screw gear part 230A and a second screw gear part 230B. A first separation (distance) between first screw gear part 230A and second screw part 230 defines slot 131. Similarly, a second separation (distance) between first screw gear part 230A and second screw part 230 defines a second slot 432. Screw gear 130, as noted above, is sometimes referred to as a hollow slotted screw gear. Screw gear 130 has a longitudinal axis that is coincident with the longitudinal axis of the handle.

Screw Gear Drive Assembly 140

FIG. 5A is an oblique view of screw gear drive assembly 140 including a proximal end surface 501. FIG. 5B is an oblique view of screw gear drive assembly 140 including a distal end surface 502.

FIG. 6 is an oblique view of contoured screw drive grip 241 including a distal end surface 602. In one example, contoured screw drive grip 241 is made from an elastomeric polymer. In one example, the elastomeric polymer has a 40 to 50 Shore A Durometer. The diameters of the inner surfaces of contoured screw drive grip 241 are selected so that graft cover advance nut 242 can be inserted into contoured screw drive grip 241, and so that after being inserted, graft cover advance nut 242 does not move relative to contoured screw drive grip 241 under normal user grasping forces. The outside contour of the outer surface is a cylindrical diameter decreasing from distal end surface 602 toward its opposite end.

Figure 7A:
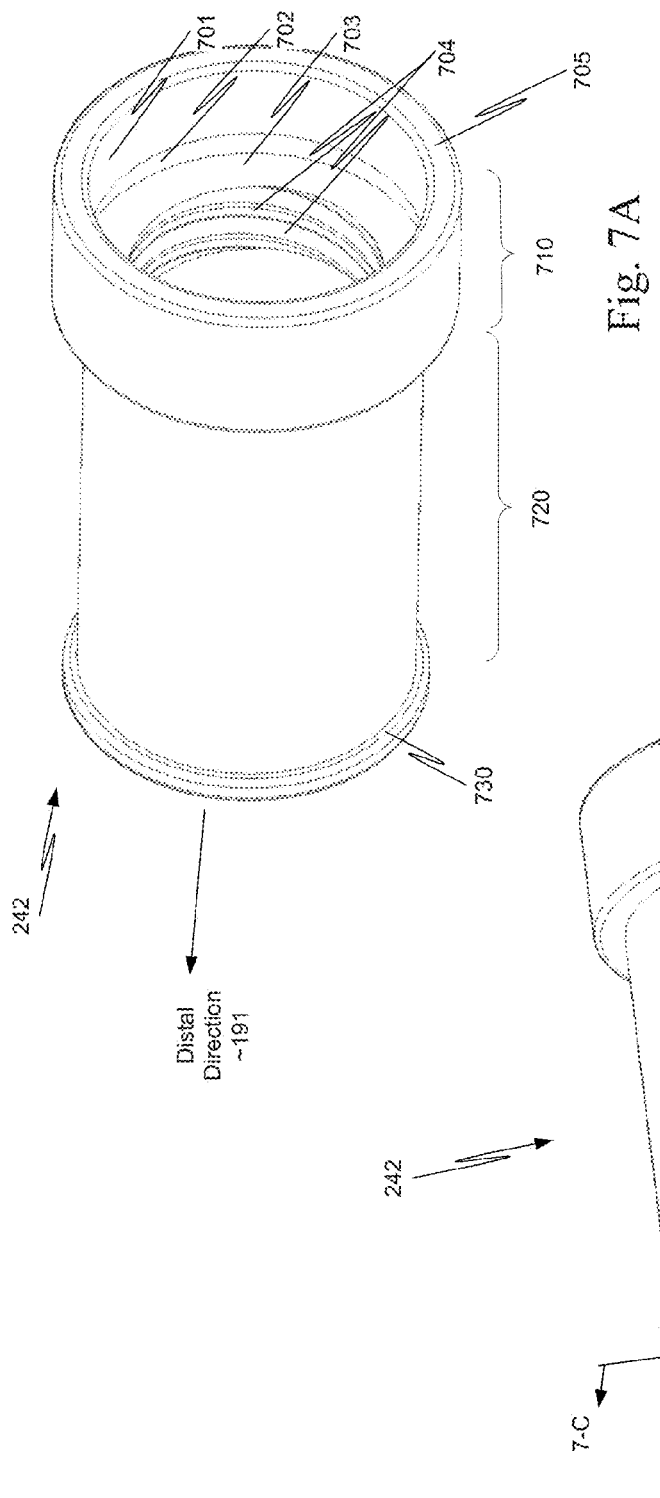
FIG. 7A is an oblique see through view of the graft cover advance nut including a proximal end surface.
Figure 7B:
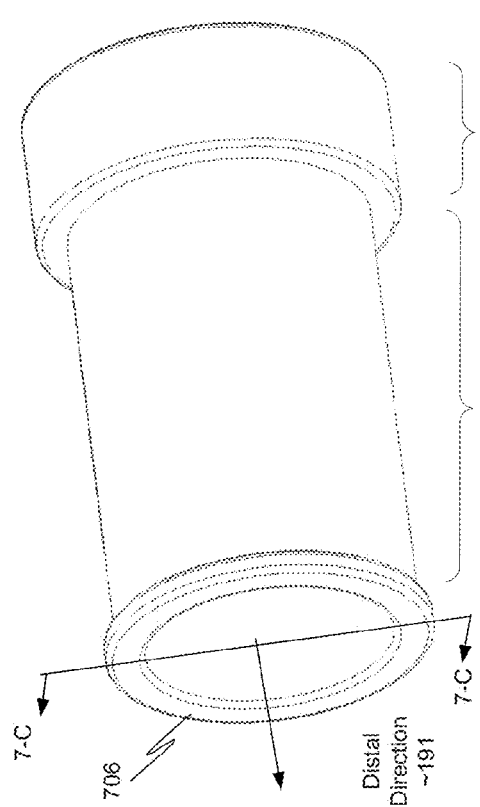
FIG. 7B is an oblique see through view of the graft cover advance nut including a distal end surface.

FIG. 7A is an oblique view of graft cover advance nut 242 including a proximal end surface 705. FIG. 7B is an oblique view of graft cover advance nut 242 including a distal end surface 706. FIG. 7C is a cross sectional view of graft cover advance nut 242 along a cut line 7C-7C in FIG. 7B. In one example, graft cover advance nut 242 is a single integral part that is formed using a mold.

In this example, a body of graft cover advance nut 242 includes a proximal body portion 710, which has a first inner surface, an intermediate body portion 720 which includes a second inner surface having a plurality of threads 704, and a distal body portion 730. (See FIGS. 7A to 7C.) The outer surface of each of these body portions is a cylindrical circumferential surface. An outer diameter 720_OD of intermediate body portion 720 (FIG. 7C) is less than an outer diameter 730_OD of distal body portion 730. Outer diameter 730_OD of distal body portion 730 is less than outer diameter 710_OD of proximal body portion 710.

In this example, proximal body portion 710 is a hollow cylinder having an axis aligned with longitudinal axis 390. However, the use of a cylindrical shape for the outside surface of proximal body portion 710 is illustrative only and is not intended to be limiting. For example, the outside surface of proximal body portion 710 could be a different geometric shape such as a hexagon or a square with an inner circular circumferential surface having an inner diameter of 710_ID.

Irrespective of the shape of the outer surface of proximal body portion 710, proximal body portion 710 includes an inner circumferential surface 701 that bounds a volume. The first inner surface is inner circumferential surface 701. The proximal end of the volume is open, while a portion of the distal end of the volume is bounded by a proximal end edge surface 703 with an open threaded hole therein.

In the example of FIG. 7C, a recessed groove 702 is formed in inner circumferential surface 701 at the distal end of inner circumferential surface 701. Proximal end edge surface 703 extends from the bottom of recessed groove 702 to the outer diameter of a bore for a plurality of threads 704 formed on an inner circumferential surface, the second inner surface, of graft cover advance nut 242 distal to proximal end edge surface 703. Proximal end edge surface 703 is a proximal end edge surface of graft cover advance nut 242, and therefore of screw gear drive assembly 140. Proximal end edge surface 703 contacts graft cover anchor assembly 150, when drive and quick release assembly 120 is being moved in proximal direction 192 using screw gear drive assembly 140.

Inner diameter 710_ID is selected so that a distal end portion of graft cover anchor 252 fits in the volume bounded by inner circumferential surface 701 of proximal end portion 710 of graft cover advance nut 242. Threads 704 extend around the inner circumferential surface of graft cover advance nut 242 and engage with screw gear 130. Distal end portion 730 is a rib extending radially outward from the outer cylindrical circumferential surface of intermediate portion 720 to prevent contoured screw drive grip 241 from coming off easily.

Graft Cover Anchor Assembly 150

FIG. 8 is an oblique view of graft cover anchor assembly 150. FIG. 9 is an oblique view of contoured graft cover release grip 251. In one example, contoured graft cover release grip 251 is made from an elastomeric polymer. In one example, the elastomeric polymer has a 40 to 50 Shore A Durometer. The diameters of the inner surfaces of contoured graft cover release grip 251 are selected so that the grasping of graft cover anchor 252 can be inserted into contoured graft cover release grip 251, and so that after being inserted, graft cover anchor 252 does not move relative to graft cover release grip 251 under normal user grasping forces.

FIG. 10A is an oblique view of graft cover anchor 252 including a distal end edge surface 1005 of outer body 1010. FIG. 10B is an oblique distal end view of graft cover anchor 252 including a distal end edge surface 1005 of outer body 1010. FIG. 10C is another oblique view of graft cover anchor 252 including a proximal end of inner body 1020. In one example, graft cover anchor 252 is a single integral part that is formed using a mold.

In this example, outer body 1010 of graft cover anchor is a hollow cylinder with a longitudinal axis coincident with longitudinal axis 390. A plurality of cantilevered beams 1013A, 1013B is formed in the hollow cylindrical outer body 1010. Each of cantilevered beams 1013A, 1013B extends distally from a proximal end portion 1010P of outer body 1010 to distal end edge surface 1005. A side edge surface of one cantilevered beam 1013A, 1013B is separated from a corresponding side edge surface of another cantilevered beam 1013B, 1013A by a slot 1014A, 1014B.

In this example, each cantilevered beam 1013A, 1013B includes a rib 1012A, 1012B extending radially outward on the outer surface of that cantilevered beam. Each rib 1012A, 1012B is positioned so that when graft cover anchor 252 is inserted in contoured graft cover release grip 251, a distal circumferential side edge surface of each rib 1012A, 1012B is adjacent a distal end edge surface of contoured graft cover release grip 251. See FIG. 8. The portion of each cantilevered beam 1013A, 1013B distal to rib 1012A, 1012B is configured to extend into the volume in the interior of proximal portion 710 of screw gear drive assembly 140 when screw gear drive assembly 140 and graft cover anchor assembly 150 are in contact. (See FIGS. 1, 2, and 3A.)

In this example, an optional engagement tab 1015A, 1015B is located on the outer surface at the distal end of each of cantilevered beams 1013A, 1013B. The radial height of engagement tab 1015A, 1015B from the outer surface of body 1010 is zero at each of slots 1014A, 1014B and gradually increases to a maximum high at the center arc of each cantilevered beam 1013A, 1013B.

Engagement tabs 1015A, 1015B latch in recessed groove 702 of graft cover advance nut 242 (FIG. 7C), when the portion of each cantilevered beam 1013A, 1013B distal to rib 1012, 1012B is inserted into the volume within the proximal end of graft cover advance nut 242. When engagement tabs 1015A, 1015B are latched in recessed groove 702 and the user grasps graft cover anchor assembly 150, the radially inward component of the force resulting from the grasp compresses (flexes) cantilevered beams 1013A, 1013B radially inward so that engagement tabs 1015A, 1015B are disengaged from recessed groove 702. Thus, when graft cover anchor assembly 150 is grasped, assembly 150 can be slid in proximal direction 192 to retract graft cover 105 more quickly than is possible using screw gear drive assembly 140 in combination with graft cover anchor assembly 150.

Outer body 1010 is outside and radially removed from screw gear 130. However, a first spacer 1031 (rib) extends from outer body 1010 through one of the slots 131, 432 (FIG. 4) in screw gear 130 to inner body 1020 that is located inside screw gear 130. Similarly, a second spacer 1032 extends from outer body 1010 through the other of slots 131, 432 in screw gear 130 to inner body 1020. First spacer 1031 has a width (thickness) W that fills one slot in screw gear 130, while second spacer 1032 has a same width W that fills the other slot in screw gear 130.

Thus, first spacer 1031 and second spacer 1032 maintain a minimum spacing between first screw gear part 230A and second screw gear part 230B and act as a structural member to prevent them from flexing (or bending) toward one another as graft cover anchor assembly 150 is slid longitudinally along screw gear 130. First and second spacers 1031, 1032 maintain a proper spacing between screw gear parts 230A, 230B.

Inner body 1020 is also a hollow cylinder with a longitudinal axis coincident with longitudinal axis 390. A retaining plug 1040 extends from a proximal end of inner body 1020. A hemostasis seal 1101 (FIG. 11) is mounted on retaining plug 1040. A center passage 1021 extends through inner body 1020 from a distal end surface of body 1020 to the proximal end of retaining plug 1040. The proximal portion of graft cover 105 is anchored in center passage 1021.

In one example, graft cover anchor 252 is molded to graft cover 105. The technique described for anchoring the graft cover to graft cover anchor 252 is illustrative only and is not intended to be limiting. Other graft cover anchors can be used having the characteristics described, except a different technique is used for securing the graft cover, sometimes referred to as a sheath, to the graft cover anchor.

FIG. 11 is a cross-sectional view of the distal portion of the handle in FIG. 2 along a cut plane extending through the longitudinal centerline of both slots 131, 432 and including longitudinal axis 390. The elements within graft cover 105 are removed in FIG. 11 for clarity.

In FIG. 11, engagement tabs 1015A, 1015B are latched in recessed groove 702. Also, distal end edge surface 1005 is in contact with proximal end edge surface 703 so that as screw gear drive assembly 140 is rotated about screw gear 130, the resulting longitudinal force of graft cover advance nut 242 on graft cover anchor 252 moves graft cover anchor assembly 150 along screw gear 130.

The use of recessed grove 702 and engagement tabs 1015A, 1015B is optional. FIG. 12 is a cross-sectional view of an alternative example of a distal portion of the handle. Graft cover 105_12, strain relief element 101_12, screw gear drive assembly 140_12 and graft cover anchor assembly 150_12, with the exceptions described below, are equivalent to graft cover 105, strain relief element 101, screw gear drive assembly 140 and graft cover anchor assembly 150, respectively.

Graft cover advance nut 242_12 is the same as graft cover advance nut 242 except graft cover advance nut 242_12 does not have recessed groove 702. Similarly, graft cover anchor 252_12 is the same as graft cover anchor 252, in one example, except, graft cover anchor 252_12 does not includes engagement tabs 1015A, 1015B at the distal end of the outer body. Also, in some examples, the cantilevered beams are not needed and therefore are not used and the outer body of graft cover anchor 252_12 is a solid hollow cylinder.

Screw gear drive assembly 140_12 functions in a manner equivalent to that described above for screw gear drive assembly 140 and so the functionality is not repeated here. Similarly, graft cover anchor assembly 150_12 functions in a manner equivalent to that described above for graft cover anchor assembly 150, except any radial force component associated with the grasping of graft cover anchor assembly 150_12 is not needed to disengage graft cover anchor assembly 150_12 from screw gear drive assembly 140_12.

In both FIGS. 11 and 12, the components making up the graft cover retractor each have a longitudinal axis that is coincident with the shown longitudinal axis of the handle. Also, in both FIGS. 11 and 12, the portion of the assembly below the axis is a mirror image of the portion of the assembly above the axis, i.e., for these cross sections there is symmetry about the longitudinal axis.

A method of operating a graft delivery system includes the steps of grasping a distal portion of a drive and quick release assembly and rotating the drive and quick release assembly in a first rotational direction along a screw gear to longitudinally move a graft cover in a first direction and changing the grasping to a proximal portion of the drive and quick release assembly and sliding only the proximal portion of the drive and quick release assembly longitudinally along the screw gear.

While the embodiments according to the invention have been described, persons skilled in the art will understand that changes and variation of those specifically described embodiments will fall in the scope and spirit of that described.

I claim:
1. A graft delivery system comprising:
   a graft cover retractor including:
   a hollow slotted screw gear including an outer surface, and threads extending from the outer surface;
   a hollow graft cover advance nut having:
   a first inner surface;
   a second inner surface distal to the first inner surface;
   a proximal end edge surface positioned between the first inner surface and the second inner surface; and
   threads extending from the second inner surface, wherein the hollow slotted screw gear is mounted within the hollow graft cover advance nut so that threads of the hollow slotted screw gear engage the threads of the hollow graft cover advance nut; and
   a spacer graft cover anchor affixed to a graft cover and having a distal end configured to removably fit within a proximal end of the hollow graft cover advance nut between threads of the hollow slotted screw gear and the first inner surface of the hollow graft cover advance nut, wherein the spacer graft cover anchor is slidable relative to the hollow graft cover advance nut,
   wherein when the distal end of the spacer graft cover anchor is within the proximal end of the hollow graft cover advance nut and is in contact with the proximal end edge surface of the hollow graft cover advance nut, and the hollow graft cover advance nut is rotated about the hollow slotted screw gear in a first rotational direction, the graft cover is retracted; and
   when the distal end of the spacer graft cover anchor is within the proximal end of the hollow graft cover advance nut and the spacer graft cover anchor is slid in a proximal direction longitudinally relative to the hollow graft cover advance nut and along the hollow slotted screw gear, the distal end of the spacer graft cover anchor is removed from within the proximal end of the hollow graft cover advance nut, and the graft cover also is retracted by the sliding.

2. The graft delivery system of claim 1 wherein the hollow graft cover advance nut is a single integral part.

3. The graft delivery system of claim 1 wherein the hollow slotted screw gear further comprises:
   a first screw gear part; and
   a second screw gear part,
   wherein a first separation between the first screw part and the second screw gear part defines at least one longitudinal slot and a second separation between the first screw part and the second screw gear part defines a second longitudinal slot.

4. The graft delivery system of claim 3 wherein the spacer graft cover anchor further comprises:
   an outer body extending around the hollow slotted screw gear;
   an inner body positioned inside the hollow slotted screw gear, and anchored to the graft cover;
   a first spacer extending through the at least one longitudinal slot, and connecting the inner body to the outer body; and a second spacer extending through the second longitudinal slot, and connecting the inner body to the outer body.

5. The graft delivery system of claim 4 wherein the spacer graft cover anchor is a single integral part.

6. The graft delivery system of claim 4 wherein the outer body further comprises:
a proximal end portion, wherein the first and second spacers extend from the proximal end portion of the outer body to the inner body.

7. The graft delivery system of claim 6 wherein the outer body further comprises:
a plurality of cantilevered beams, wherein each cantilevered beam extends in a distal direction from the proximal end portion of the outer body, and includes a distal end, and further wherein the distal end of the spacer graft cover anchor assembly comprises the distal end of the cantilevered beam.

8. The graft delivery system of claim 7 wherein each cantilevered beam further comprises:
an engagement tab at the distal end of the cantilevered beam, wherein the engagement tab extends radially out from an outer surface of the cantilevered beam.

9. The graft delivery system of claim 8, wherein the proximal end of the hollow graft cover advance nut includes:
a proximal portion having:
an inner circumferential surface bounding a volume wherein the inner circumferential surface is the first inner surface,
wherein the proximal end edge surface is located at a distal end of the volume, and
a proximal end of the volume is open, wherein the second inner surface and the threads extending from the second inner surface are distal to the proximal end edge surface of the graft cover advance nut.

10. The graft delivery system of claim 9, wherein the hollow graft cover advance nut includes:
a recessed groove formed in the inner circumferential surface adjacent to and proximal to the proximal end edge surface of the hollow graft cover advance nut, wherein the engagement tab at the distal end of the cantilevered beam latches in the recessed groove so that a distal end edge surface of the cantilevered beam contacts the proximal end edge surface of the hollow graft cover advance nut.

11. The graft delivery system of claim 6 wherein the outer body further comprises:
a hollow cylinder, extending distally from the proximal end portion of the outer body, having a distal end, wherein the distal end of the spacer graft cover anchor assembly comprises the distal end of the hollow cylinder.

12. The graft delivery system of claim 11, wherein the proximal end of the hollow graft cover advance nut includes:
a proximal portion having:
an inner circumferential surface bounding a volume wherein the inner circumferential surface is the first inner surface,
wherein the proximal end edge surface is located at a distal end of the volume, and
a proximal end of the volume is open, wherein the second inner surface and the threads extending from the first inner surface are distal to the proximal end edge surface of the graft cover advance nut.

13. The graft delivery system of claim 12, wherein when the distal end of the hollow cylinder is inserted in the volume of the graft cover advance nut, a distal end edge surface of the hollow cylinder contacts the proximal end edge surface of the graft cover advance nut.

14. A graft delivery system comprising:
a graft cover retractor including:
(i) a hollow screw gear including:
a first screw gear part; and
a second screw gear part,
wherein a first separation between the first screw part and the second screw gear part defines a first longitudinal slot and a second separation between the first screw part and the second screw gear part defines a second longitudinal slot;
(ii) a screw gear drive assembly mounted on the screw gear comprising:
a hollow graft cover advance nut including:
a proximal portion having:
a proximal end edge surface; and
a first inner surface comprising a circumferential surface bounding a volume,
wherein the proximal end edge surface is located at a distal end of the volume, and
a proximal end of the volume is open; and
a plurality of screw gear teeth formed on a second inner surface of the graft cover advance nut, wherein the second inner surface is distal to the proximal end edge surface of the graft cover advance nut; and
(iii) a spacer graft cover anchor having:
an outer body, extending around the screw gear, including a distal end edge configured to be removably positioned within the volume;
an inner body, positioned within the hollow screw gear, affixed to a graft cover;
a first spacer extending through the first longitudinal slot, and connecting the inner body to the outer body; and
a second spacer extending through the second slot, and connecting the inner body to the outer body;
wherein the spacer graft cover anchor is slidable relative to the hollow graft cover advance nut, and when (i) the distal end of the spacer graft cover anchor is within the proximal end of the hollow graft cover advance nut and is in contact with the proximal end edge surface of the hollow graft cover advance nut, and (ii) the hollow graft cover advance nut is rotated about the hollow screw gear in a first rotational direction, the graft cover is retracted; and
when the distal end of the spacer graft cover anchor is within the proximal end of the hollow graft cover advance nut and the spacer graft cover anchor is slid in a proximal direction longitudinally relative to the hollow graft cover advance nut and along the hollow screw gear, the distal end of the spacer graft cover anchor is removed from within the proximal end of the hollow graft cover advance nut, and the graft cover also is retracted by the sliding.

15. The graft delivery system of claim 14 wherein the spacer graft cover anchor is a single integral part; and the hollow graft cover advance nut is a single integral part.

16. The graft delivery system of claim 14 wherein the outer body further comprises:
a plurality of cantilevered beams, wherein each cantilevered beam extends in a distal direction from a proximal end portion of the outer body, and includes a distal end edge surface, and further wherein the distal end edge surface of the outer body abutting the proximal end edge surface of the graft cover advance nut comprises the distal end edge surface of the cantilevered beam.

17. The graft delivery system of claim 16 wherein each cantilevered beam further comprises:

an engagement tab at a distal end of the cantilevered beam, wherein the engagement tab extends radially out from an outer surface of the cantilevered beam.

18. The graft delivery system of claim 17, wherein the graft cover advance nut further comprises:
a recessed groove formed in the inner circumferential surface adjacent to and proximal to the proximal end edge surface of the graft cover advance nut, wherein the engagement tab at the distal end of the cantilevered beam latches in the recessed groove so that the distal end edge surface of the cantilevered beam contacts the proximal end edge surface of the graft cover advance nut.

19. The graft delivery system of claim 14 wherein the outer body further comprises:
a hollow cylinder, extending distally from a proximal end portion of the outer body, having a distal end edge surface, wherein the distal end edge surface of the outer body abutting the proximal end edge surface of the screw gear drive assembly comprises the distal end edge surface of the hollow cylinder.

* * * * *